United States Patent
De Vleeschauwer et al.

(10) Patent No.: US 8,679,770 B2
(45) Date of Patent: Mar. 25, 2014

(54) **SERUM BACTERICIDAL ASSAY FOR *N. MENINGITIDIS* SPECIFIC ANTISERA**

(75) Inventors: Isabel De Vleeschauwer, Rixensart (BE); Nathalie Durant, Rixensart (BE); Jan Poolman, Rixensart (BE); Vincent Weynants, Rixensart (BE)

(73) Assignee: Glaxo Smith Kline Biologicals S.A., Rixensart (BE)

( * ) Notice: Subject to any disclaimer, the term of this patent is extended or adjusted under 35 U.S.C. 154(b) by 833 days.

(21) Appl. No.: 12/065,682

(22) PCT Filed: Sep. 5, 2005

(86) PCT No.: PCT/EP2005/009566
§ 371 (c)(1),
(2), (4) Date: Mar. 4, 2008

(87) PCT Pub. No.: WO2007/028408
PCT Pub. Date: Mar. 15, 2007

(65) Prior Publication Data
US 2008/0220457 A1    Sep. 11, 2008

(51) Int. Cl.
*G01N 33/569* (2006.01)
(52) U.S. Cl.
USPC .......................... 435/7.32; 435/810; 435/975
(58) Field of Classification Search
None
See application file for complete search history.

(56) References Cited

U.S. PATENT DOCUMENTS

2008/0064057 A1    3/2008  De Vleeschauwer et al.

FOREIGN PATENT DOCUMENTS

WO    2004/014417    2/2004
WO    2004/103400    12/2004

OTHER PUBLICATIONS

Susan E. Maslanka, et al., *Standardization and a multilaboratory comparison of Neisseria meningitidis serogroup A and C serum bactericidal assays*, Clinical & Diagnostic Laboratory Immunology, vol. 4:2, 156-167 (1997). XP002375515. ISSN: 1071-412X.

D. M. Granoff, et al., *Immunogenicity of an investigational quadrivalent Neisseria meningitidis-diphtheria toxoid conjugate vaccine in 2-year-old children*, Vaccine, Butterworth Scientific, Guilford, GB, vol. 23:34, 4307-4314 (Jul. 29, 2005). XP004973252. ISSN: 0264-410X.

K. B. J. Donaldson, et al., *Evaluation of strains and optimal incubation times in Neisseria meningitidis serogroup A and C serum bactericidal assays*, Abstracts of the Gen. Meeting of the Am. Soc'y for Microbiology, vol. 95: 0, 293 (1995). XP009064727 & 95th Gen. Meeting of the Am. Soc'y for Microbiology, Washington, D.C., USA, May 21-25, 1995. ISSN: 0160-2011.

Y. Almazrou, et al., *Serologic responses to ACYW135 polysaccharide meningococcal vaccine in Saudi children under 5 years of age*, Infection & Immunity, vol. 73: 5, 2932-2939 (May 2005). XP002375514. ISSN: 0019-9567.

*Primary Examiner* — Padma V Baskar
(74) *Attorney, Agent, or Firm* — Virginia G. Campen (57) ABSTRACT

The present invention relates to the field of Serum Bactericidal Activity (SBA) assays for Gram negative bacteria, in particular *N. meningitidis*. The SBA assay is the most important method for measuring functional activity of serum antibodies against meningococcus. In order to determine whether a subject or a population is seropositive against invasive meningococcus the SBA test should ideally be both sensitive and specific. The inventors have found the standard *N. meningitidis* serotype A and W SBAs can be significantly improved in this regard.

9 Claims, 1 Drawing Sheet

Figure 1

1. Multimark
2. GalE
3. L8
4. L3
5. MenA CDC F8328.
6. MenA A1.
7. MenA 3227.
8. MenA 3048.
9. MenA 760570.
10. Multimark

Figure 2

SERUM BACTERICIDAL ASSAY FOR *N. MENINGITIDIS* SPECIFIC ANTISERA

This application is filed pursuant to 35 U.S.C. §371 as a United States National Phase Application of International Patent Application Ser. No. PCT/EP2005/009566 filed Sep. 5, 2005, the content of which is incorporated herein by reference.

FIELD OF THE INVENTION

The present invention relates to the field of neisserial vaccine compositions, and methods to assess the quality of the immune response elicited after their administration, for instance laboratory correlates of protection, and in particular serum bactericidal activity (SBA).

BACKGROUND OF THE INVENTION

*Neisseria meningitidis* (meningococcus) is a Gram negative bacterium frequently isolated from the human upper respiratory tract. It is a cause of serious invasive bacterial diseases (on an endemic and epidemic scale) such as bacteremia and meningitis. The incidence of meningococcal disease shows geographical, seasonal and annual differences (Schwartz, B., Moore, P. S., Broome, C. V.; Clin. Microbiol. Rev. 2 (Supplement), S18-S24, 1989). The bacterium primarily affects children from 6 months to 2 years, but also affects teenagers. The bacterium is commonly classified according to the serogroup of its capsular polysaccharide.

Most disease in temperate countries is due to strains of serogroup B and varies in incidence from 1-10/100,000/year total population—sometimes reaching higher values (Kaczmarski, E. B. (1997), Commun. Dis. Rep. Rev. 7: R55-9, 1995; Scholten, R. J. P. M., Bijlmer, H. A., Poolman, J. T. et al. Clin. Infect. Dis. 16: 237-246, 1993; Cruz, C., Pavez, G., Aguilar, E., et al. Epidemiol. Infect. 105: 119-126, 1990).

Epidemics dominated by serogroup A meningococci, mostly in central Africa, sometimes reach incidence levels of up to 1000/100,000/year (Schwartz, B., Moore, P. S., Broome, C. V. Clin. Microbiol. Rev. 2 (Supplement), S18-S24, 1989). Nearly all cases as a whole of meningococcal disease are caused by serogroup A, B, C, W-135 and Y meningococci, and a tetravalent A, C, W-135, Y capsular polysaccharide vaccine is available (Armand, J., Aminjon, F., Mynard, M. C., Lafaix, C., J. Biol. Stand. 10: 335-339, 1982). The available polysaccharide vaccines are currently being improved by way of chemically conjugating them to carrier proteins (Lieberman, J. M., Chiu, S. S., Wong, V. K., et al. JAMA 275: 1499-1503, 1996). The serogroup B capsular polysaccharide has been found to be nonimmunogenic—most likely because it shares structural similarity with host components (Wyle, F. A., Artenstein, M. S., Brandt, M. L. et al. J. Infect. Dis. 126: 514-522, 1972; Finne, J. M., Leinonen, M., Mäkelä, P. M. Lancet ii.: 355-357, 1983).

The frequency of *Neisseria meningitidis* infections has risen in the past few decades in many European countries. This has been attributed to increased transmission due to an increase in social activities under crowded conditions (for instance discos, swimming pools, theatres, etc.). It is no longer uncommon to isolate *Neisseria meningitidis* strains that are less sensitive or resistant to some of the standard antibiotics. This phenomenon has created an unmet medical need and demand for new anti-microbial agents, vaccines, drug screening methods, and diagnostic tests for this organism.

The development of effective vaccines requires reliable tests for establishing whether an effective immune response has been elicited in vaccinated individuals. For *N. meningitidis* serogroup A, B and C vaccines Serum Bactericidal Activity (SBA) assays are seen as being the gold standard in the field (with a four-fold increase in SBA being accepted as surrogates for protection for these serogroups) [Borrow et al., 2001, Infect Immun 69:1568-1573; Vermont et al., 2002, FEMS Immun and Med Microbiol 34:89-96]. The assay can give information on: a) whether any particular serum sample has a level (titre) of bactericidal antibodies sufficient to reach a protective threshold, b) a % seropositivity (% SP) of subjects surpassing this level, c) a % seroconversion (% SC) of subjects either i) with a ratio of SBA titres (post- to pre-immunisation sera titres) which increase beyond a particular multiple (4-fold), or ii) as for % SP if the level of SBA titres pre-immunisation in the subjects (i.e. the very young) is below the protective SBA threshold. This assay is therefore used as a primary read-out (of protection and vaccine efficacy). In addition to SBA assays IgG ELISA assays are often used as a secondary readout. These ELISA assays measure the concentration (in μg/ml) of IgG antibodies in a serum sample which bind to a meningococcal capsular polysaccharide (A, C, W135 or Y).

In A, C, W135 (or W), and Y SBA assays the effect of respectively specific anti-serogroup A, C, W and Y *Neisseria meningitidis* antibodies are evaluated in the presence of complement (typically from baby rabbit [a rSBA assay], or alternatively from human sera [a hSBA assay]). A mixture of bacteria and complement is added to the sera. The meningococcal specific antibodies bind to the target cell-surface via meningococcal-specific protein or carbohydrate moieties. The C1q subunit of C1 binds to the Fc portion of the surface-bound Ig. The binding of C1q to Ig activates the classical pathway of the complement which ultimately results in death of the target cell. The bactericidal titre for each serum is expressed as the reciprocal serum dilution corresponding to 50% killing.

SBA assay methods are well-known in the art. In 1976 WHO Expert Committee on Biological Standardization recommended an SBA assay to be used to satisfy the requirements for production and release of meningococcal polysaccharide vaccines (WHO Tech. Rep. Ser. 1976, 594:72-73). Since this time Centers for Disease Control and Prevention (CDC), Atlanta, Ga., USA has researched into the various variables in an SBA assay (No. of CFU per well, assay buffer, growth of the target strain, assay incubation time, source of complement, complement concentration, and starting dilution of serum) and has recommended standard SBA assay protocols well-known and used in the field (Maslanka et al. Clin, Diag. Laboratory Immun. 1997, 4:156-167). Typically the CDC also recommends and provides meningococcal strains to be used in SBA assays in the meningococcal vaccine field. For instance for *N. meningitidis* serogroup C (MenC) SBA assay (WHO guidelines) a consensus has been reached with regard to the recommended assay strain to use.

SUMMARY OF THE INVENTION

As stated above the SBA assay is the most important method for measuring functional activity of serum antibodies against meningococcus. In order to determine whether a subject or a population is seropositive against invasive meningococcus (or has seroconverted post vaccination) the SBA test should ideally be both sensitive and specific. It should be sensitive to protective antibodies induced post immunization with effective vaccines (such as MenA/W/C/Y capsular saccharide conjugate vaccines) but not merely to complement not in the presence of antibodies. It should also be specific so that it registers the presence of functional antibodies against invasive strains, but minimizes the effect of the presence of any low avidity antibodies that might be effective against carriage strains but not against invasive strains.

The present inventors have found that the SBA methods currently employed to assess protective antibodies against meningococcal serogroups A and W135 can be significantly improved in one or more of the above respects.

For *N. meningitidis* serogroup A (MenA) a particular CDC strain is recommended for SBA assays (F8238)—see Maslanka et al., supra. The inventors have found in a clinical trial, however, that although SBA assays employing this strain may determine the protective immune response caused by vaccination (with a MenA capsular saccharide conjugate vaccine) around 5 months of age, SBA assays using the strain did not efficiently differentiate the responses pre- and post-immunization at a later age (10-15 months). The inventors have found that natural immunity to MenA strains can start to occur between 1 and 2 years of age by the recognition of epitopes on carrier isolates (primarily of the L11 LOS immunotype). This is due in large part to an immune response against non-capsular polysaccharide antigens, and in particular due to natural lipooligosaccharide (LOS) immunization, and possibly low-avidity antibodies against capsular polysaccharide antigens. Surprisingly, it has also been determined that the CDC-approved MenA SBA strain (F8238) predominantly expresses L11 epitopes.

There is therefore a significant problem in the use of conventional CDC-approved MenA assays for evaluating MenA capsular saccharide vaccine compositions. The present inventors have developed advantageous SBA strategies using novel MenA reference strains. The present inventors have also developed SBA strategies that may be implemented in general for all Gram negative bacteria that have LOS as a component which may lead to natural immunity such that efficacy of a vaccine composition may be differentiated from natural immunity against LOS epitopes from bacteria isolated from asymptomatic carriers.

In addition the inventors have surprisingly found that the strain provided/suggested by the CDC for *N. meningitidis* serogroup W-135 (MenW) SBA assays (strain S4383) is not optimal for this purpose in that it is too sensitive to being killed by the complement source itself without having serum present. This poses significant problems in the use of this strain for SBA assays. Again advantageous SBA strategies using novel MenW reference strains have been developed.

Accordingly there is provided in one embodiment a *N. meningitidis* serogroup A or serotype W Serum Bactericidal Activity (SBA) assay (e.g. a hSBA or rSBA assay) comprising the step of determining the SBA titre of a serum sample against, respectively, a *N. meningitidis* serogroup A or serotype W reference strain having the following characteristics:

a) it has a % complement toxicity of less than 40%, 35, 30, 20, 10, 5%, or is around 0%, and/or that its % complement toxicity is less than that of the MenW S4383 standard strain available from the Centers for Disease Control and Prevention, Atlanta, Ga., USA or from the BCCM;

b) the % seropositivity against the strain in a group of at least 25 naïve 1-2 year old children where seropositivity is measured by an rSBA assay with titres of 8 or above (to achieve 50% cell killing) is less than 40, 35, 30, 25, 20 or 15%, and/or the % seropositivity against the strain in a group of at least 25 naïve 1-2 year old children where seropositivity is measured by an rSBA assay with titres of 8 or above (to achieve 50% cell killing) is less than that of the % seropositivity against the F8238 standard strain available from the Centers for Disease Control and Prevention, Atlanta, Ga., USA or from the BCCM; and c) the % seroconversion against the strain in a group of at least 25 3-5 year old children immunized with a unconjugated *N. meningitidis* ACWY capsular polysaccharide vaccine is more than 50, 60, 70, 80, 90 or 95%, where seroconversion is measured by assessing the % of subjects with at least a 4 fold increase in rSBA titre (to achieve 50% cell killing) when sera is compared just before immunization (when they are naïve) and one month after immunization with the vaccine.

The MenA reference strain in one embodiment is an invasive strain of L10 immunotype. Strain 3125 is well suited for the MenA SBA assays of the invention. Strain 3193 (W135: 2a:P1.5,2:L3) is well suited for the MenW SBA assays of the invention.

In a further aspect of the invention there is provided a Serum Bactericidal Activity (SBA) assay for a Gram negative bacterium comprising the step of determining the SBA titre of a serum sample against said Gram negative bacterium, wherein before use the serum sample is depleted of antibodies against lipooligosaccharide (LOS) epitopes present in said Gram negative bacterium.

This is achieved in one embodiment by preincubating the serum sample with one or more lipooligosaccharide (LOS) epitopes (and preferably the entire LOS molecule) present in the Gram negative bacterium to deplete the serum sample of antibodies against the LOS epitopes. In particular this approach is useful for MenA, where serum samples can be advantageously removed of anti-L10 and/or L3,7,9 and/or L1,8 antibodies and/or anti-L11 antibodies, by incubation with each respective LOS epitope/molecule.

Furthermore, kits for carrying out the SBA assays of the invention are provided, as is the use of the above strains of the invention in an SBA assay.

DESCRIPTION OF THE INVENTION

The subject matter of and information disclosed within the publications and patents or patent applications mentioned in this specification are incorporated by reference herein.

Reference to "lipooligosaccharide" (or "LOS") may also be referred to as "lipopolysaccharide" or "LPS". Reference to an LOS epitope of a particular immunotype is also reference to a complete LOS molecule of the particular immunotype.

The terms "comprising", "comprise" and "comprises" herein is intended by the inventors to be optionally substitutable with the terms "consisting of", "consist of", and "consists of", respectively, in every instance.

The SBA assays of the invention as mentioned herein can either be rSBA (using baby rabbit complement) or hSBA (using human complement) assays except where it is clear from the test that a particular type is specified.

As stated above, the SBA assay is the most important method for measuring functional activity of serum antibodies against meningococcus. To date SBA has proved to be the best surrogate of protection against meningococcus (it correlates highly with immunity to meningococcal disease). Typically 'pre' and 'post' immunization sera are collected from a naïve subject (for instance 'pre' collected from the subject just before vaccine administration [never having been immunized with a vaccine comprising the antigen in the vaccine previously], and 'post' 1 month post immunization) and bactericidal dilution titres to meningococcal strains are determined by an hSBA assay (e.g. see Borrow et al., 2005 Vaccine 23:2222-2227) or an rSBA assay according to the CDC protocol [e.g. the MSG96 protocol] (Maslanka et al., supra). Bactericidal titres for pre- and post-immunization sera are expressed as the reciprocal of the dilution resulting in 50% killing of the bacteria (either the 2-fold serum dilution corresponding to at least 50%, or determined exactly by a mathematical fit from a series of 2-fold serum dilutions) as compared to the number of target cells present before incubation with serum and complement (for instance if the bacteria are in the presence of active complement but without serum). The assay can give information on: a) whether any particular 'pre' or 'post' serum sample has a level (titre) of bactericidal antibodies sufficient to satisfy the correlate of protection (usually this is a titre of >=4 in an hSBA assay, or >=8 for a rSBA assay [Borrow et al., 2005, supra], b) a % seropositivity (% SP) of subjects in a study (typically at least 25, e.g. at least 50) pre- and/or post-vaccination with >=the relevant serum correlate level, c) a Geometric Mean Titre (GMT) of all (typically at least 25, e.g. at least 50) the 'post' (and 'pre' if relevant) SBA titres in a vaccine study d) a % seroconversion (% SC) of subjects in a study (typically at least 25, e.g. at least 50) with either: i) a ratio of SBA titres (post-to pre-immunisation sera SBA titres) which increase beyond a particular level (usually >=to a 4 fold increase in SBA titres post immunisation) [typically used for adults where natural immunity may have raised 'pre' SBA titres beyond the correlate of protection level]; or ii) % subjects (typically at least 25, e.g. at least 50) post-vaccination with >=the relevant serum correlate level (typically used for very young children).

Serum Bactericidal Activity (SBA) assays for Gram negative bacteria are provided in this invention. Suitable methods of carrying out SBA assays are well known to a skilled person (e.g. see Maslanka et al., supra and Examples 1 and 2 herein for optimized Nmen assays). Such assays involve testing a serum sample (pre- and post-immunisation for instance) for the titre required to cause a 50% cell killing against the Grain negative bacterium.

In one embodiment of the invention (as described above) a *N. meningitidis* serogroup A or serotype W Serum Bactericidal Activity (SBA) assay comprising the step of determining the SBA titre of a serum sample against, respectively, a *N. meningitidis* serogroup A or serotype W reference strain having the following beneficial characteristics over strains used in the prior art for such purposes (for instance strains recommended by the CDC):

a) i) it has a % complement toxicity of less than 40%, 35, 30, 20, 10, 5%, or is around 0%, and/or ii) that its % complement toxicity is less than that of the MenW S4383 standard strain;

b) i) the % seropositivity against the strain in a group of at least 25 naïve 1-2 year old children where seropositivity is measured by an rSBA assay with titres of 8 or above (to achieve 50% cell killing) is less than 40, 35, 30, 25, 20 or 15%, and/or ii) the % seropositivity against the strain in a group of at least 25 naïve 1-2 year old children where seropositivity is measured by an rSBA assay with titres of 8 or above (to achieve 50% cell killing) is less than that of the % seropositivity against the F8238 standard strain; and c) the % seroconversion against the strain in a group of at least 25 3-5 year old children immunized with a unconjugated *N. meningitidis* ACWY capsular polysaccharide vaccine is more than 50, 60, 70, 80, 90 or 95%, where seroconversion is measured by assessing the % of subjects with at least a 4 fold increase in rSBA titre (to achieve 50% cell killing) when sera is compared just before immunization (when they are naïve) and one month after immunization with the vaccine.

Any permutation of the above characteristics is envisaged by the inventors. In particular for any embodiment of the invention with a combination of charactistics a) and b) the following combinations of charactistics are specifically envisioned:

| a)i) <40% | a)i) <35% | a)i) <30% | a)i) <20% | a)i) <10% | a)i) <5% | a)i) 0% | a)ii) |
|---|---|---|---|---|---|---|---|
| b)i) <40% | b)i) <40% | b)i) <40% | b)i) <40% | b)i) <40% | b)i) <40% | b)i) <40% | b)i) <40% |
| a)i) <40% | a)i) <35% | a)i) <30% | a)i) <20% | a)i) <10% | a)i) <5% | a)i) 0% | a)ii) |
| b)i) <35% | b)i) <35% | b)i) <35% | b)i) <35% | b)i) <35% | b)i) <35% | b)i) <35% | b)i) <35% |
| a)i) <40% | a)i) <35% | a)i) <30% | a)i) <20% | a)i) <10% | a)i) <5% | a)i) 0% | a)ii) |
| b)i) <30% | b)i) <30% | b)i) <30% | b)i) <30% | b)i) <30% | b)i) <30% | b)i) <30% | b)i) <30% |
| a)i) <40% | a)i) <35% | a)i) <30% | a)i) <20% | a)i) <10% | a)i) <5% | a)i) 0% | a)ii) |
| b)i) <25% | b)i) <25% | b)i) <25% | b)i) <25% | b)i) <25% | b)i) <25% | b)i) <25% | b)i) <25% |
| a)i) <40% | a)i) <35% | a)i) <30% | a)i) <20% | a)i) <10% | a)i) <5% | a)i) 0% | a)ii) |
| b)i) <20% | b)i) <20% | b)i) <20% | b)i) <20% | b)i) <20% | b)i) <20% | b)i) <20% | b)i) <20% |
| a)i) <40% | a)i) <35% | a)i) <30% | a)i) <20% | a)i) <10% | a)i) <5% | a)i) 0% | a)ii) |
| b)i) <15% | b)i) <15% | b)i) <15% | b)i) <15% | b)i) <15% | b)i) <15% | b)i) <15% | b)i) <15% |
| a)i) <40% | a)i) <35% | a)i) <30% | a)i) <20% | a)i) <10% | a)i) <5% | a)i) 0% | a)ii) |
| b)ii) | b)ii) | b)ii) | b)ii) | b)ii) | b)ii) | b)ii) | b)ii) |

Each of these may be separately combined with more than 50, 60, 70, 80, 90 or 95% from characteristic c). Characteristic c) should be assessed using any unconjugated *N. meningitidis* ACWY capsular polysaccharide vaccine e.g. Mencevax™ from GlaxoSmithKline Biologicals s.a. or the like. This should be assessed in subjects over the age of 3 (e.g. between the ages of 3 and 5, or between the ages of 18 and 25).

With respect to characteristic a)ii) in the embodiments of the invention "less than" that of the standard strain can mean at least 10, 20, 30, 40 or 50% complement toxicity units fewer than the % complement toxicity for the standard strain.

With respect to characteristic b)ii) in the embodiments of the invention "less than" that of the standard strain can mean at least 10, 20, 30, 40 or 50% seropositivity units fewer than the % seropositivity for the standard strain.

Characteristic b)ii) may optionally be replaced herein by the characteristic that the ratio of % seropositivity (carried out as described by b)ii)) of the 3125 strain to the unknown reference strain is 0.1-2.5, 0.5-2.0, 0.7-1.5, or around 1 (0.9-1.1).

The reference strain characteristic a), b) or c) [or a) and b), a) and c), b) and c), or a), b) and c)] can be suitably assessed by carrying out the % complement toxicity and/or the % seropositivity and/or the % seroconversion measures, respectively, as described in Example 2b, 1b and 1c, respectively.

In a further aspect of the invention there is provided a N. meningitidis serogroup W Serum Bactericidal Activity (SBA) assay comprising the step of determining the SBA titre of a serum sample against a N. meningitidis serogroup W reference strain, wherein the N. meningitidis serogroup W reference strain is not sensitive to complement dependent killing in the absence of serum, or at least less sensitive to complement dependent killing in the absence of serum than the S4383 standard reference strain available from the Centers for Disease Control and Prevention, Atlanta, Ga., USA or from the BCCM. For instance the % Complement Toxicity for the N. meningitidis serogroup W reference strain may be less than 40%, 35, 30, 20, 10, 5%, or is around 0%. The term "less than" that of the standard strain can mean at least 10, 20, 30, 40 or 50% complement toxicity units fewer than the % complement toxicity for the standard strain. Optionally the reference strain also has characteristic c) as described above.

The sensitivity of the N. meningitidis serogroup W reference strain to complement dependent killing can be ascertained by measurement of % complement toxicity by the method of Example 2b.

The sensitivity of the N. meningitidis serogroup W reference strain used in the assay to complement dependent killing is ascertainable by using a control in the absence of sera in any suitable SBA assay known in the art (e.g. see Maslanka et al., supra). For instance the SBA assay of Example 2b may be used (where % complement toxicity is measured). The colony forming units (CFUs) obtained for this control are thus the result of the growth of bacteria without addition of human serum sample, the average of the obtained CFUs for reference strains should therefore ideally correspond to 0% killing.

In particular % Complement Toxicity is a useful assessment of the complement sensitivity of a MenW strain, or any SBA reference strains discussed herein. This can be calculated if a further SBA control takes place with only diluent, bacteria and inactivated complement [e.g. after heat treatment—such as 40 minutes at 56° C. before use] (instead of the active complement in the first control) is added to the plates. Ideally 8 or more (e.g. 48) pairs of active and inactive samples are measured to obtain an average measurement. Each active/inactive pair of measurements can be with the same lot of complement source or with different lots, though within each pair the same lot of complement should be used. Any complement source can be used which is suitable for SBA assays (such as baby rabbit complement). The bacterial killing obtained in the samples using active complement is compared with the bacterial killing obtained in the samples using inactivated complement. The results are expressed as % Complement Toxicity by calculating:

$$\% \text{ Complement Toxicity} = \frac{\text{Average\# } CFU \text{ Inactivated Complement} - \text{Average\# } CFU \text{ Active Compliment} * 100\%}{\text{Average\# } CFU \text{ Inactivated Complement}}$$

The % Complement Toxicity for the MenW strain obtained from the CDC for SBA assays—S4383—for instance was around 55% in one experiment.

In typical SBA assays plates are rejected where the % Complement Toxicity control on the plate exceeds 40% (otherwise very high SBA titres would be obtained and a high variability of the results). The present invention can overcome this problem and may lead to a reduction in loss of such wasted plates.

In a still further aspect of the invention there is provided a N. meningitidis serogroup A Serum Bactericidal Activity (SBA) assay comprising the step of determining the SBA titre of a serum sample against a N. meningitidis serogroup A reference strain having the following characteristic:

b)i) the % seropositivity against the strain in a group of at least 25 naïve 1-2 year old children where scropositivity is measured by an rSBA assay with titres of 8 or above (to achieve 50% cell killing) is less than 40, 35, 30, 25, 20 or 15%, or b)ii) the % seropositivity against the strain in a group of at least 25 naïve 1-2 year old children where seropositivity is measured by an rSBA assay with titres of 8 or above (to achieve 50% cell killing) is less than that of the % seropositivity against the F8238 standard strain. The % seropositivity measure may optionally be carried out as described in Example 1b. Optionally the reference strain also has characteristic c) as described above.

With respect to characteristic b)ii) in the embodiments of the invention "less than" that of the standard strain can mean at least 10, 20, 30, 40 or 50% seropositivity units fewer than the % seropositivity for the standard strain.

Characteristic b)ii) may optionally be replaced herein by the characteristic that the ratio of % seropositivity (carried out as described by b)ii)) of the 3125 strain to the unknown reference strain is 0.1-2.5, 0.5-2.0, 0.7-1.5, or around 1 (0.9-1.1).

In general for the N. meningitidis serogroup A or serotype W Serum Bactericidal Activity (SBA) assays of the invention for characteristic b) the at least 25 naïve 1-2 year old children may be native to the Philippines. For the N. meningitidis serogroup A Serum Bactericidal Activity (SBA) assays of the invention, the N. meningitidis serogroup A reference strain can be an invasive strain, and can optionally be of immunotype L10 (or predominantly this immunotype), for instance strain 3125, or can optionally be of immunotype L3,7,9 (or predominantly this immunotype), for instance strain 3048. Optionally the group A strain Z1092 (4,21:P1.10) from Marc Achtman (Max-Planck Institut fur Infektionsbiologie, Berlin, Germany) [Granoff et al. 2005 Vaccine 23:4307-4314] is not a MenA reference strain of the invention, For the N. meningitidis serogroup W Serum Bactericidal Activity (SBA) assays of the invention, the N. meningitidis serogroup W reference strain can be an invasive strain, and can optionally be of immunotype L3,7,9 (or predominantly this immunotype), for instance strain 3193. Optionally the group W-135 strain M9262 (2a:P1.5,2) from US Centers for Disease Control and Prevention (CDC) [Granoff et al. 2005 Vaccine 23:4307-4314] is not a MenW reference strain of the invention. Clearly the F8238 and S4383 strains are not SBA standard strains of the above aspects of the invention.

In the N. meningitidis serogroup A or serotype W Serum Bactericidal Activity (SBA) assays of the invention the serum sample may be taken from a host immunized with a vaccine composition comprising a capsular saccharide (oligosaccharide or polysaccharide) antigen (preferably conjugated to a carrier protein) from N. meningitidis serogroup A and/or W.

In the N. meningitidis serogroup A or serotype W Serum Bactericidal Activity (SBA) assays of the invention the serum sample may have been taken from a human aged 0-55 years, 1 month-20 years, 2 months-16 years, 6 months-10 years, 8 months-7 years, 10 months-4 years, 0-2 years, 6 months-2 years, or 1-2 years.

A kit is also provided for carrying out the SBA assays of the invention. In such a kit the reference strain(s) of the invention may be provided. This could be provided along with necessary instructions of use in an SBA assay, and optionally other SBA assay reagents.

The use of the reference strains of the invention (and in particular *N. meningitidis* W135:2a:P1.5,2:L3 isolate 3193 from the Netherlands Reference Laboratory for Bacterial Meningitis, Amsterdam [of from ECACC]—the % Complement Toxicity for this strain was found to be very low [around −9% in one experiment]—or *N. meningitidis* A:NT:P1.6: L3,6 isolate 3048 from the Netherlands Reference Laboratory for Bacterial Meningitis, Amsterdam [or from ECACC], or an invasive L10 *N. meningitidis* serogroup A strain [such as isolate 3125], or strains with similar attributes as described herein) in a SBA assay is a further aspect of this invention.

The inventors have further found that it is at least in part an antibody response against LOS from carriage strains of Gram negative bacteria (e.g. meningococcus e.g. of serogroup A) that can lead to high apparent SBA titres in sera from naïve children aged 1-2 years old.

Therefore in a further aspect of the invention there is provided a Serum Bactericidal Activity (SBA) assay for a Gram negative bacterium comprising the step of determining the SBA titre of a serum sample against said Gram negative bacterium, wherein before use the serum sample is depleted of antibodies against lipooligosaccharide (LOS) epitopes present in said Gram negative bacterium. By "depleted" it is meant that antibodies against at least one immunotype of LOS is reduced in concentration by 20, 30, 40, 50, 60, 70, 80, 90, 95 or 100%.

The serum sample may have been taken from naïve host (not immunized with a vaccine composition comprising antigens from said Gram negative bacterium) or from a host that has been so immunized (e.g. one month before serum collection) with a vaccine composition not comprising LOS antigens from the Gram negative bacterium, and wherein the SBA titre is measured with reference to the Gram negative bacterium which comprises an antigen present in the vaccine composition. For instance, the vaccine composition may comprise a capsular saccharide (oligosaccharide or polysaccharide) antigen (preferably conjugated to a carrier protein such as tetanus toxoid, diphtheria toxoid, CRM197, protein D from *H. influenzae*, etc.) from the Gram negative bacterium.

In one embodiment the Serum Bactericidal Activity (SBA) assay of the invention is performed such that before use the serum sample has been preincubated with one or more lipooligosaccharide (LOS) epitopes or one or more immunotypes of LOS molecule of said Gram negative bacterium to deplete said serum sample of antibodies against said LOS epitopes/immunotypes. By "LOS epitopes" it is meant that oligosaccharide structures present on the LOS responsible for the LOS immunotype are used, or mimotopes thereof, or even the entire LOS molecule is used.

In one embodiment the one or more LOS epitopes/immunotypes used to deplete the serum sample comprise one or more LOS epitopes/immunotypes which predominate in carriage strains of the Gram negative bacterium. By "predominate" it is meant that over 10, 20, 30, 40, 50 or 60% of the carriage strains of the bacterium comprise the epitope.

It is envisioned that the SBA assays of the invention will be applicable to any Gram negative bacterium SBA assay where the Gram negative bacterium has LOS. In one embodiment, it will be of use in SBA assays for neisserial strains, for instance *Neisseria meningitidis* serogroup A, B, C, W or Y, in particular serogroup A (MenA).

In such a neisserial SBA assay before use the serum sample can be preincubated with LOS epitopes derived from one or more LOS immunotypes, or with one or more LOS immunotypes, selected from the group consisting of: L1, L2, L3, L4, L5, L5, L6, L7, L8, L9, L10, L11, and L12. For instance a preincubation step may be done with L11 (the most common immunotype of MenA carriage strains) and/or L3,7,9 and/or L10 and/or L1 and/or L8 and/or L2.

Pre-incubation can be readily achieved by, for instance, incubating sera samples for 1 hour at 37° C. with a 100 μg/ml solution of LOS (a V/V mix can be made thus giving a final concentration of 50 μg/mL LOS).

Meningococcal lipooligosaccharides (LOS) are outer membrane bound glycolipids which differ from the lipopolysaccharides (LPS) of the Enterobacteriaceae by lacking the O side chains, and thus resemble the rough form of LPS (Griffiss et al. Rev Infect Dis 1988; 10: S287-295). Heterogeneity within the oligosaccharide moiety of the LOS generates structural and antigenic diversity among different meningococcal strains (Griffiss et al. Inf. Immun. 1987; 55: 1792-1800). This has been used to subdivide the strains into 12 immunotypes described above (Scholtan et al. J Med Microbiol 1994, 41:236-243). Immunotypes L3, L7, & L9 are immunologically identical and are structurally similar (or even the same) and have therefore been designated L3,7,9 (or, for the purposes of this specification, generically as "L3"). Meningococcal LOS L3,7,9 (L3), L2 and L5 can be modified by sialylation. Antibodies to LOS have been shown to contribute to the bactericidal activity in children infected with *N. meningitidis* (Griffiss et al J Infect Dis 1984; 150: 71-79).

In a further embodiment of the invention the LOS preincubation step is added to any or all the SBA assays described herein (e.g. using the meningococcal serogroup A or W reference strains of the invention).

A kit is also provided for carrying out this SBA assay of the invention comprising means for depleting a serum sample of antibodies against LOS (for instance those means described above) and instructions for its use in an SBA assay. The LOS epitopes (preferably entire LOS) for preincubating sera and/or reference strains of the invention may be provided in the kit. Necessary instructions of use, and optionally other SBA assay reagents may also be included. Methods of isolating LOS from bacteria of appropriate immunotype are well known in the art (see for instance the hot water-phenol procedure of Wesphal & Jann [Meth. Carbo. Chem. 1965, 5:83-91]). See also Galanos et al. 1969, Eur J Biochem 9:245-249, and Wu et al. 1987, Anal Bio Chem 160:281-289. Such methods can be used to make the LOS included in the kits of the invention.

Alternatively, the effect of carriage strains on anti-LOS antibodies in naïve hosts may be removed as an SBA assay issue if the SBA assay strain did not cross-react with anti-LOS antibodies. Thus in a still further aspect of the invention a Serum Bactericidal Activity (SBA) assay for a Gram negative bacterium is provided comprising the step of determining the SBA titre of a serum sample against a Gram negative bacterium reference strain which is a LOS mutant either unable to synthesise LOS or which produces a truncated LOS oligosaccharide structure (such that the strain is not sensitive to anti-LOS antibodies in sera samples). For meningococcus, for instance, an lpxX mutant or other known mutants may be used to remove LOS.

Alternatively, highly truncated LOS structures can be produced in lgtA(−), lgtE(−) or galE(−) strains which may be used as reference strains in any or all of the SBA assays of the invention. A kit is also provided for carrying out this SBA assay of the invention comprising such a mutant reference strain, and instructions for its use in an SBA assay.

The examples below are carried out using standard techniques, which are well known and routine to those of skill in the art, except where otherwise described in detail. The examples are illustrative, but do not limit the invention.

EXAMPLES

Example 1a

A Typical MenA SBA Assay Procedure (e.g. using the 3125 or F8238 Men A Strain as the Reference Strain)

Day Change
Day 1 1. Pre-culture of the Working Seed
   Working Seed Men A 3125 [or F8238](−70° C.).
   Spread 50 μL of bacteria in isolation way across the following plates:
   3 brain heart infasion+1% horse serum (BHI) (4° C.).
   1 thayer Martin (TM)→selective media for Nmen with Antibiotic (4° C.). [control plate which showing *N. meningitidis* cells are present]
   1 nutrient agar (NA)→detection of the contamination (4° C.). [control plate showing there is no contaminants growing—Nmen should not grow]
   Incubate overnight or for approximately 40-42 hours at 37° C., 5% CO2 with humidity for colonies to grow.
Day 2 2. Culture of the WS on Solid Media
   Control the TM and NA media: verify before the test.
   Take about 20 colonies (well isolated) of 1 BHI petri dish.
   Spread these colonies across 1 BHI, repeat this operation 3 times.
   Incubate during 4 hours at 37° C., 5% CO2 with humidity.
3. Samples and Controls Preparation
   (serum samples and controls are inactivated for 40 min at 56° C. before use) Dilutions in tube with assay diluent PBS+glucose 0.1%+$MgCl_2$ 0.5 mM+$CaCl_2$ 0.9 mM pH 7.4 (4° C.).

| CTRL1: (−20° C.) | dil: 1/32 in tube (1/128 in microplate). |
| CTRL2: (−20° C.) | dil: 1/128 in tube (1/512 in microplate. |

(CTRL1/2 are optional controls of serum samples with known SBA titres)

| Samples 1/8 in microplate: | dil: 1/2 in tube. |
| Samples 1/256 in microplate | dil 1/64 in tube. |

4. Sample and Control Addition
   4.1. Assay Diluent Addition (in Sterile Microplate Nunc 96 Wells Flat Bottom, with Microptates Lids)
   Diluent: PBS+glucose 0.1%+$MgCl_2$ 0.5 mM+$CaCl_2$ 0.9 mM pH7.4.
   Distribute 25 μL of diluent in each well of the microplate.
   4.2. Sample and Control Addition
   Distribute 25 μL of sample and control into the first row, column 1 to 5 and 7 to 11.
   Mix the solutions in the first row.
   Transfer 25 μL from A to B. Repeat the transfers from B to C, . . . , row G to H.
   After mixing the serum in row H, remove 25 μL and discard.
   Distribute 25 μL of sample into the column 12, sample 1 into the well A, . . . , 8 into the well H.
   Mix.
   After mixing, remove 25 μL and discard.

5. Bacterial Suspension Preparation
51. Harvest Colonies from 1 BHI with 5 mL of Assay Diluent.
   Dilute this suspension with assay diluent to obtain an OD of +/−0.400 (0.380-0.420) at 600 nm.
5.2. Bacterial Suspension
   Prepare a 1:175000 dilution of bacterial suspension [approx. 114 CFU/25 μl]:
   1:10: 1 mL 0.400 absorbance+9 mL assay diluent dil (1:10).
   1:100: 1 mL of 1:10 solution+9 mL assay diluent dil (1:10).
   1:1000: 1 mL of 1:100 solution+9 mL assay diluent dil (1:10).
   1:175000: 2 mL of 1:1000 solution+33 mL assay diluent dil (1:17.5).
6. Bacteria/Complement Mixture Addition
   Rabbit complement Pel Freez (−70° C.) [e.g. complement from 3-4 week old baby rabbits]
   Thawing of the inactive and active complement is done at room temperature.
   Prepare the mixtures of bacteria with inactive and active complement corresponding to 50% of complement and 50% bacterial suspension 1:175000.
   Add 25 μL of the inactive mixture into the column 12.
   Add 25 μL of the active mixture into the column 1 to 11.
   Cover the microplates with plastic film.
   Incubate during 1 hour 30 at 37° C. in the orbital shaker (210 rpm).
Day 3 7. Addition of the Agar Medium
   Liquefy the agar medium in a microwave and equilibrate its temperature in a water-bath (48° C.).
   Remove the plastics from the plates and change the microplates lids.
   Coat 1: Add 50 μL of the TSB [Tryptic Soy Broth]+0.9% agar (4° C.).
   Leave the microplates under the flow-hood at room temperature during 15' to solidify the agar.
   Coat 2: Add 50 μL of the TSB+0.9% agar (4° C.).
   Leave the microplates under the flow-hood at room temperature during 30' (or 15 minutes if sufficient time) to solidify the agar.
   Incubate 16-20 (or 18-20) hours at 33° C. with humidity (without CO2).
   Thus rows A to H correspond to 8 2 fold dilutions of sera sample (e.g. from 8 to 1024; or starting at 64 if the serum is known to have high titres), except for lane 6 which is the blank (0% killing: bacteria+active complement but no serum) and lane 12 (bacteria with the eight serum samples at lowest dilution+Inactive complement [40 min at 56° C. before use]). Lanes 7 and 8 are optional control serum samples of known bactericidal titre. Lanes 1-5, 9-11 are the 8 test serum samples on the plate.
8. Reading of the Plates and Data Transfer
   Remove the microplates lids.
   CFUs in each well are counted by any method know in the art, for instance the plates can be read with the KS400 imaging system (Zeiss): MA1 protocol.
   Transfer of the raw data and calculation of titres with SoftMax pro.
   The bactericidal titer for each serum is expressed as the reciprocal serum dilution corresponding to 50% killing (relative to the 0% killing control [blank] of bacteria+active complement only—i.e. 50% killing=50% of the average CFU for all such controls on a plate).

Example 1b

Typical Method to Calculate % Seropositivity

Carry out the method of Example 1a or 2 with the chosen reference strain with sera from at least 25 (for instance at least 50) different naïve children between the ages of 1 and 2 (when protective immunity is low in the majority of such children).

To look at the specificity of the SBA assay, sera from naïve children [i.e. who have not been vaccinated with a MenA and/or MenW vaccine (for instance a capsular saccharide conjugate)], the sera can be assessed for SBA titres achieving 50% cell killing. The % of these subjects with sera achieving a reciprocal titer equal to or more than 8 in the SBA test is defined as % seropositivity.

% seropositivity post immunization with MenA and/or MenW vaccine can also be done in this way.

Example 1c

Typical Method to Calculate % Seroconversion

Carry out the method of Example 1a or 2 with the chosen reference strain with sera from at least 25 (for instance at least 50) different children (naïve Dust prior to immunization] and one month post immunization with a unconjugated *N. meningitidis* ACWY capsular polysaccharide vaccine e.g. Mencevax™ from GlaxoSmithKine Biologicals s.a.) over the age of 3 (e.g. between the ages of 3 and 5, or between the ages of 18 and 25).

To assess the sensitivity of the SBA assay, the % seroconversion against the strain is measured by assessing the % of subjects with at least a 4 fold increase in rSBA titre (to achieve 50% cell killing).

Example 2

A Typical MenW SBA Assay Procedure (Using 3193 Strain as the Reference Strain for Example)

Day Change
Day 1 1. Samples and Controls Preparation
(samples and controls are inactivated during 40 min at 56° C. before use) Dilutions in tube with assay diluent PBS+ glucose 0.1%+$MgCl_2$ 0.5 mM+$CaCl_2$ 0.9 mM pH7.4 (4° C.).

| | |
|---|---|
| CTRL1: (−20° C.) | dil: 1/128 in tube (1/512 in microplate). |
| CTRL2: (−20° C.) | dil: 1/128 in tube (1/512 in microplate). |

(CTRL1/2 are optional controls of serum samples with known SBA titres)

| | |
|---|---|
| Samples 1/8 in microplate: | dil: 1/2 in tube. |
| Samples 1/256 in microplate | dil 1/64 in tube. |

2. Sample and Control Addition
2.1. Assay Diluent Addition (in Sterile Microplate Nunc 96 Wells Flat Bottom, with Microplates Lids)
Diluent: PBS+glucose 0.1%+$MgCl_2$ 0.5 mM+$CaCl_2$ 0.9 mM pH7.4.
Distribute 25 μL of diluent in each well of the microplate.

2.2. Sample and Control Addition
Distribute 25 μL of sample and control into the first row, column 1 to 5 and 7 to 11.
Mix the solutions in the first row.
Transfer 25 μL from A to B. Repeat the transfers from B to C, . . . , row G to H.
After mixing the serum in row H, remove 25 μL and discard.
Distribute 25 μL of sample into the column 12, sample 1 into the well A, . . . , 8 into the well H.
Mix.
After mixing, remove 25 μL and discard.
3. Bacterial Suspension Preparation
Working Seed Men W135 3193 (−70° C.).
3.1. Subculture of the Working Seed.
25 μL is spread across 1 TM plate and 1 NA plate in massive way (control media).
Incubate overnight at 37° C., 5% CO2 with humidity.
3.2. Bacterial Suspension
Prepare a 1:18000 dilution of bacterial suspension (no sub-culture needed: the bacterial suspension is made directly by diluting the working seed (WS) up to 1:18000 [OD600 of the WS=between 0.400-0.500]; the diluted bacterial suspension contains approx. 1111 CFU/25 μl):
1:10: 200 μL WS+1800 μL assay diluent (1:10).
1:100: 1 mL of 1:10 solution+9 mL assay diluent (1:10).
1:1000: 1 mL of 1:100 solution+9 mL assay diluent (1:10).
1:18000: 2 mL of 1:1000 solution+34 mL assay diluent (1:18).
4. Bacteria/Complement Mixture Addition
Rabbit Complement Pel Freez (−70° C.) [e.g. Complement from 3-4 Week Old Baby Rabbits]
Thawing of the inactive and active complement is done at room temperature. Prepare the mixtures of bacteria with inactive and active complement corresponding to 60% of complement and 40% bacterial suspension 1:18000.
Add 25 μL of the inactive mixture into the column 12.
Add 25 μL of the active mixture into the column 1 to 11.
Cover the microplates with plastic film.
Incubate during 1 hour at 37° C. in the orbital shaker (210 rpm).
5. Addition of the Agar Medium
Liquefy the agar medium in a microwave and equilibrate it's temperature in a water-bath (48° C.).
Remove the plastics from the plates and change the microplates lids.
Coat 1: Add 100 μL of the TSB+0.9% agar (4° C.).
Leave the microplates under the flow-hood at room temperature to solidify the agar (approx. 30 minutes).
Coat 2: Add 25 μL of the TSB+0.9% agar (4° C.).
Leave the microplates under the flow-hood at room temperature to solidify the agar (15 min).
Incubate 18-20 hours at 35° C. with humidity (without $CO_2$).
Day 2 6. Reading of the Plates and Data Transfer
Control the TM and NA media.
CFUs in each well are counted by any method know in the art, for instance the plates can be read with the KS400 imaging system (Zeiss): MA1 protocol.
Transfer of the raw data and calculation of titres with SoftMax pro.
The bactericidal titer for each serum is expressed as the reciprocal serum dilution corresponding to 50% killing (relative to the 0% killing control [blank] of bacteria+ active complement only—i.e. 50% killing=50% of the average CFU for all such controls on a plate).

Example 2b

Calculation of Complement Toxicity

The bactericidal titre for each unknown serum is expressed as the reciprocal serum dilution corresponding to exactly 50% killing of the bacteria. The 0% killing (i.e. maximum CFUs) is obtained through the blank. The blank in the GSK rSBA assay contains only diluent, bacteria and active complement.

In order to test the complement toxicity of a strain, a simplified SBA assay (compared to [but based on] Examples 1a and 2) can be set up where only blanks comprising diluent, bacteria and active complement are compared with controls comprising diluent, bacteria and inactivated complement on the plate. The CFUs obtained in wells filled with diluent, bacteria and active complement are then compared to the CFUs obtained in wells filled with diluent, bacteria and inactivated complement (40 min at 56° C. before use). In a 96 well plate 8 or more of each should be tested, for instance 48 of each. The CFUs of all active samples can be averaged and compared with the average CFUs or inactive complement samples using the following formula:

$$\frac{\% \text{ Complement}}{\text{Toxicity}} = \frac{\text{Average\# } CFU \text{ Inactivated Complement 1} - \text{Average\# } CFU \text{ Active Compliment 1}}{\text{Average\# } CFU \text{ Inactivated Complement 1}} * 100$$

We have found that *Neisseria meningitidis* strains with a % complement toxicity comparable to that of MenW 3193 strain (i.e. around 0%) have beneficial % complement toxicity properties for use in SBA assays (see Example 4).

Example 3

MenA SBA Assay Results

It is known that natural immunity may play an important role for the protection against *Neisseria meningitidis* A.

In a recent clinical study performed in the Philippines in which infants were primed with a menA conjugate vaccine a non-primed group was added as a control. When the children were aged 10 months it was observed that more antibodies were detected with the MenA SBA test than with the MenA IgG ELISA test (More than 70% of the infants had a MenA rSBA response, while less than 10% had a MenA IgG ELISA response in the non-primed groups). This effect may be due to several reasons: Presence of anti-PSA antibodies which are not measured by the GSK menA IgG ELISA, or presence of non-PSA antibodies induced by carriage of non-pathogenic *neisseria* or some other bacteria expressing cross-reactive surface antigens shared with meningococci.

Unimmunised subjects around 5 months old had low SBA titres (<10% with titres more than or equal to 8 using the CDC-approved F8238 strain). However pre-boost at 10 months of age unimmunised SBA went up to 77% with titres more than or equal to 8). Post-boost at 12-13 months, of the 23% unimmunised control subjects that did not have titres more than or equal to 8, 80% of these now did have such a titre. Distinguishing SBA due to immunization vs. natural immunity was thus difficult.

Presence of other than IgG anti-PSA antibodies were investigated by an anti-total Ig PSA ELISA.

Regarding the MenA strains we hypothesised that LPS was involved in natural immunity. Twelve LPS immunotypes have been described in *Neisseria meningitidis* corresponding to a diverse range of carbohydrate-structures. The L9-11 are predominantly found among serogroup A meningococci.

We endeavoured to find a way to differentiate between the immune response caused by vaccination and by natural immunity.

MenA IgTOT ELISA:

First, the presence of antibodies IgG other than anti-PSA antibodies was investigated. In the standard assay the anti-human IgG conjugate was replaced by anti-IgA+M+G conjugate. As can be seen below the concordance between the MenA IgG ELISA and the MenA SBA test is somewhat improved, but doesn't explain the observed natural immunity, consequently a further search related to assay strains and LPS inhibition was performed.

| Comparison | N | IgTOT/ELISA | Concordance IgG ELISA/SBA | Concordance IgTot ELISA/SBA |
|---|---|---|---|---|
| DTPw-HepB/HibMenAC-TT-002* (10 Mths of age) | | | | |
| Pre Challenge | 102 | 1.31 | 52% | 63% |
| Post Challenge | 97 | 1.57 | 85% | 96% |
| MenCY-PD-001 (20-24 Mths of age) | | | | |
| Pre | 16 | — | 69% | 81% |
| Post 1 (Mencevax group) | 24 | 1.85 | 96% | 100% |

*Since the booster phase of the study is still ongoing. it's not known whether subjects were primed or not.

Figure 1:
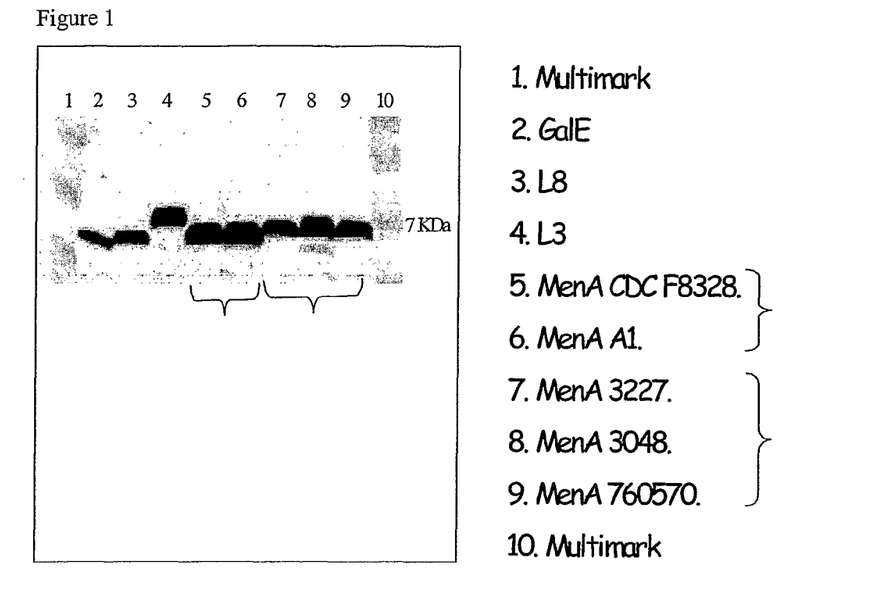
FIG. 1 depicts a tricine gel run to determine the immunotype profile of strain F8328 (=CDC F8238) strain and potential new strains isolated in the Netherlands (3227, 3048, 760570).
Figure 2:
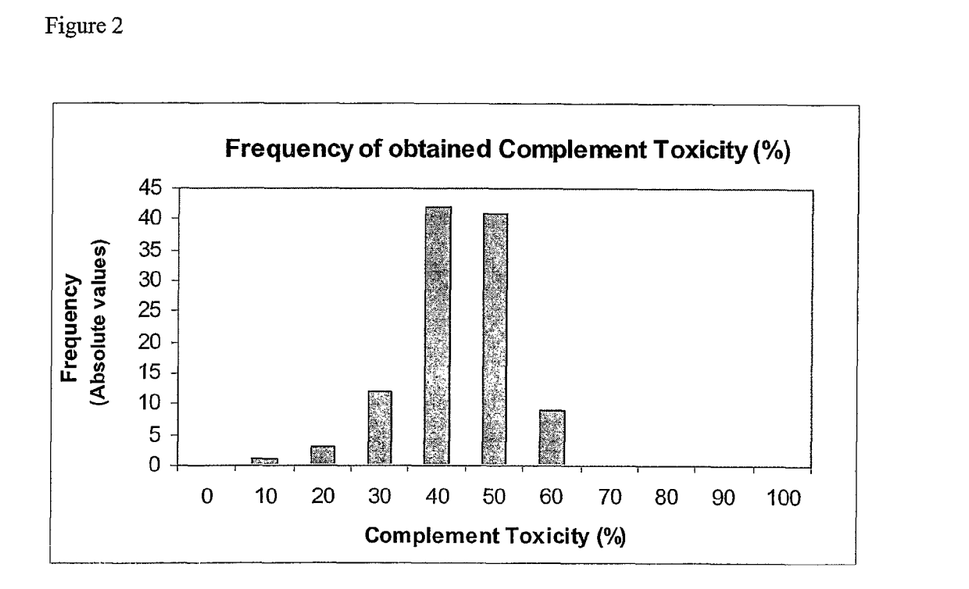
FIG. 2 graphically illustrates frequency of obtained complement toxicity.

Use of a Different MenA Assay Strain.
Two Actions with the Complete Strains:
  Tricine gels were run (FIG. 1) in order to determine the immunotype profile of the current strain ie the F8328 (=CDC F8238) strain and potential new strains isolated in the Netherlands (3227, 3048, 760570). Although the exact profile of both strains cannot be determined, the gel does indicate that both groups of strains have a different LOS profile.
  In addition an ELISA and rSBA test were run to differentiate strains. In both, the ELISA and rSBA the respective strains were used as test strain and the 9-2-L379 mouse monoclonal was used for screening. The assays indicated that F8238 seemed not to be a L3, L7 or L9 strain (actually immunotyped to be a L11 profile—see Example 5—in contrast to the L10 profile suggested by Maslanka et al., supra), while the Dutch strains were found to react. Based on complement toxicity data the 3048 strain was selected for further evaluation (Data not shown).
LPS Inhibition:
  LPS purified from MenB H44/76 was obtained and sera were inhibited with this L3 LPS. This was done by incubation for 1 hour at 37° C. with a 100 μg/ml solution (a V/V mix was made thus giving a final concentration of L3 LPS of 50 μg/mL). As seen in the attached tables a full neutralization could be obtained for the discordant serum samples mentioned above (ELISA vs rSBA), while only a partial inhibition sera could be obtained for concordant samples (ELISA vs rSBA). The discordant samples related to pre-immunization (pre-booster) samples, are expected to be highest.

| Sample | Time-Point | MenA ELISA (μg/mL) IgG | IgTOT | MenA rSBA |
|---|---|---|---|---|
| | | | | MenA rSBA After neutralization with 50 μg LOS |
| 207 | Pre | <0.30 | 0.51 | 494 | <64 |
| | P1M1 | 5.02 | 7.08 | 1466 | 474 |
| 218 | Pre | <0.30 | 0.37 | 265 | <64 |
| | P1M1 | 1.21 | 1.37 | 245 | <64 |
| 331 | Pre | <0.30 | 0.39 | 195 | <64 |
| | P1M1 | 17.05 | 25.70 | 684 | 250 |
| 337 | Pre | <0.30 | <0.30 | 371 | <64 |
| | P1M1 | 28.50 | 38.28 | 2334 | 1665 |
| 339 | Pre | <0.30 | <0.30 | 410 | <64 |
| | P1M1 | 0.60 | 1.77 | 1514 | 1112 |
| 246 | Pre | 0.77 | 1.76 | 4195 | 2960 |
| | P1M1 | 9.85 | 21.07 | 5108 | 2144 |
| 238 | Pre | 0.94 | 1.19 | 502 | <=64 |
| | P1M1 | 38.16 | 70.25 | 3333 | 2291 |
| 36 | Pre | 10.84 | 17.24 | 449 | 171 |
| | P1M1 | 27.75 | 41.22 | 1876 | 964 |
| 151 | Pre | 35.91 | 45.75 | 1245 | 386 |
| | P1M1 | 35.66 | 69.00 | 1844 | 1337 |
| | | | | | MenA rSBA After neutralization with 100 μg LOS |
| 322 | Pre | <0.30 | <0.30 | 304 | <64 |
| | P1M1 | 0.31 | 0.63 | 406 | <64 |
| 323 | Pre | <0.30 | <0.30 | 289 | <64 |
| | P1M1 | 4.16 | 5.73 | 1681 | 315 |
| 344 | Pre | <0.30 | <0.30 | 791 | <64 |
| | P1M1 | <0.30 | 0.53 | 2571 | 158 |
| 3 | Pre | 1.91 | 2.22 | 767 | <64 |
| | P1M1 | 18.34 | 19.28 | 1673 | 825 |

The crucial importance of anti-LPS in the natural immunity against menA has not been described before, and the critical use of this new information to develop assays to evaluate A PS induced response is new.

Example 4

MenW SBA Studies

INVENTION

Our proposal is to use a rSBA assay which uses the 3193 (or similar) strain and not the S4383 strain. The S4383 strain was found to be subject to complement toxicity in the GSK rSBA set-up.

Killing of *N. meningitidis* W in SBA tests should occur due to the combination of both anti-MenW antibodies in the serum sample and complement (in this case an exogeneous source of complement i.e. rabbit complement is used). To check on the intrinsic bactericidal activity of rabbit complement two controls are added in each assay. In the first control active complement is added to bacteria without antibodies, in the second control inactivated complement is added to the bacteria without antibodies (see Example 2b). Rabbit complement lots are refused in case a bactericidal effect is seen in the controls.

→The complement toxicity criteria were met with the 3193 strain but not with S4383.

BACKGROUND

Bactericidal effect should only occur when both antibodies and active complement are added in the presence of complement. To check on this, a bactericidal control with only diluent, bacteria and active complement is added in each assay. The colony forming units (CFUs) obtained for this control are thus the result of the growth of bacteria without addition of human serum sample, the average of the obtained CFUs thus corresponds to 0% killing.

When a new complement is used a second bactericidal control with only diluent, bacteria but now inactivated complement is added to the plates as well. The bacterial killing obtained in the bacterial control using active complement is then compared with the bacterial killing obtained in the bacterial complement using inactivated complement. This is done as following:

$$\% \text{Complement Toxicity} = \frac{\# CFU \text{ Inactivated Complement} - \# CFU \text{ Active Compliment}}{\# CFU \text{ Inactivated Complement}} * 100\%$$

→In case the % Complement Toxicity exceeds 40% the assay plate is rejected. Bacteria would thus be killed through addition of complement only. If this criterium were not used, this could lead to very high SBA titres and a high variability of the results.

Data 108 assay plates were tested using the classical rSBA assay set-up with the S4383 strain. On each plate both bacterial controls were added. Although when all complement toxicities obtained in the different plates are averaged a value of 39% is obtained, the figure below indicates that for many plates the 40% criterium was not met.

It was GSK's intention to adapt the assay set-up in a later stage in order to harmonize between the SBA assays. Since the complement toxicity problem occurred it was decided to harmonize the assay set-up upfront and then compare the S4383 and the 3193 strain in that assay format. Prior to further testing the complement toxicity was now compared by dividing assay plates in two parts: one part with the bacterial complement with active complement, one part with the bacterial complement with inactive complement. A complement toxicity of 55% was now obtained with the 4383 strain, −9% with the 3193 strain.

→Based on these data it was decided to continue with the 3193 strain.

Example 5

Immunotypes of MenA LOS

Recently, in non-primed toddlers a discrepancy was observed between anti-PSA IgG ELISA data and MenA bactericidal data obtained with the reference strain F8238. A significant level of MenA bactericidal antibodies were measured whilst almost no MenA PS IgG antibodies were found. These observations suggest that these children have developed a natural immunity against *Neisseria meningitidis* serogroup A. It was also suggested that this discrepancy could be linked to the use of a SBA MenA strain that expressed a LOS close or similar to the LOS of carriage MenA strains (and not similar to the LOS of invasive MenA strains).

The aim of this example is to review the literature data in order to assess if carriage and invasive serogroup A meningococci strains express or not similar LOS and to determine their major immunotypes.

Methods

Only the papers using the most accurate immunotyping methods were selected. They are the following:

Zollinger W and Mandrell R (1980)

In this paper, the immunotools are rabbit polyclonal antibodies. Based on the data discussed in the article, it can be conclude that:
- the anti-L10 is specific of the L10 immunotype,
- the anti-L11 reacts strongly against the L11 immunotype but shows some cross-reactivity against the L10 immunotype
- the anti-L9 does not react against the L10 and L11 immunotypes but shows some cross-reaction against L3, L4, L6 and L7 strains Kim JJ et al (1988) Salih M et al (1990) and Achtman M et al (1992)

These three papers were selected because they combined immunotyping and the relative molecular weights ($M_rS$) of the LOS. The LOS of *N. meningitidis* strains is composed of one to six components that can be separated by SDS-PAGE. The $M_rS$ have been estimated to be between 3150 and 7100. These different electrophoretic mobilities reflect differences in the chemical composition of their oligosaccharides and the oligosaccharide compositional differences also account for antigenic differences.

| Immunotype | $M_rS$ |
|---|---|
| L8 | 3600 |
| L9 | 4200-4500 |
| L10 | 4000 |
| L11 | 3600 |

Poolman J et al (1982) and Scholten R et al (1994).

In these two articles, microprecipitation with polyclonal antibodies and/or whole-cell ELISA typing using a set of 14 different monoclonal antibodies were used.

The microprecipitation was demonstrated to be a specific technique, whilst the assignment of immunotype using an algorithm, based on the reactivity of the 14 MAbs, gives similar results to the microprecipitation technique.

Other papers found in the literature were rejected based on absence of clear demonstration of the specificity of immunotyping methods.

Results

Immunotype of Invasive MenA Strains

The following table summarizes the data from the first four articles.

| Ref | Origin | | L379 | L10 | L11 | L10, 11 | Other | ND |
|---|---|---|---|---|---|---|---|---|
| a | China | | 2 | 7 | 6 | 0 | 0 | 1 |
|  | US | | 0 | 1 | 1 | 1 | 0 | 1 |
|  | others | | 4 | 2 | 1 | 0 | 1 |  |
| b | Sudan | | 1 | 18 | 2 | 0 | 4 | 0 |
|  | Sweden | | 9 | 5 | 9 | 0 | 2 | 0 |
| c | Africa | Subgroup III | 29 | 122 | 49 | 0 | 9 | 13 |
|  |  | Clone IV-1 | 125 | 0 | 0 | 0 | 0 | 8 |
| d | Germany | | 0 | 9 | 1 | 0 | 0 | 0 |
|  | Africa | | 7 | 5 | 0 | 0 | 0 | 0 |
|  | Finland | | 0 | 0 | 4 | 0 | 1 | 1 |
|  | Brazil | | 0 | 6 | 0 | 0 | 0 | 0 |
|  | North America | | 2 | 24 | 2 | 1 | 0 | 2 |

-continued

| Ref | Origin | L379 | L10 | L11 | L10, 11 | Other | ND |
|---|---|---|---|---|---|---|---|
| Percentage with clone IV-1 | | 35.9 | 40.0 | 15.1 | 0.4 | 3.4 | 5.2 |
| without clone IV-1 | | 14.8 | 54.5 | 20.5 | 0.5 | 4.7 | 4.9 |

* C strain isolated from carrier, D strain isolated from disease
a: Kim J et al (1988);
b: Salih M et al (1990);
c: Achtman M et al (1992);
d: Zollinger W and Mandrell R (1980)

Not taking into account clone IV-1 strains, the results show that most of invasive MenA strains are L10 (54.4%) followed by L11 in immunotype (20.5%) and L9 immunotype (14.8%). It is of note that most of the MenA strains displaying the immunotype 9 harbor also other immunotypes (most generally L3 and/or L7).

These data (from invasive MenA strains) correlate well with data obtained by microprecipitation (and/or whole cell ELISA with a panel of 14 MAbs) (Poolman et al, 1982 and Scholten et al, 1994).

| Origin | C/D* | L379 | L10 | L11 | Other | ND |
|---|---|---|---|---|---|---|
| diverse | D | 5 | 11 | 1 | 9 | 0 |

It can be concluded that most of invasive MenA strains (not including the strains belonging to clone IV-1) are L10. Others are either L9(L379) or L11.

Immunotype of Carriage MenA Strains

| Ref | Origin | L9 | L10 | L11 or L10, 11 | Other | ND |
|---|---|---|---|---|---|---|
| d | North America | 1 | 2 | 10 | 0 | 2 |
| e | Diverse | 0 | 4 | 1 | 2 | 0 |
| Percentage | | 4.5 | 27.3 | 50.0 | 9.1 | 9.1 | e: Poolman et al (1984)

Carriage strains isolated in North America are mainly L10, 11 immunotype. Nevertheless as the anti-L11 rabbit polyclonal used for this typing cross-reacts with L10, it is not possible to conclude if these strains display or not the L10 immunotype.

Interestingly, the limited data obtained from carriage MenA strains seems to indicate that immunotype distribution among these strains is quite different to the distribution observed for invasive cases. Indeed, if most of invasive strains are L10, the majority of carriage strains express at least the L11 immunotype.

Conclusion And Discussion

The classical MenA SBA developed by the CDC used the F8238 strain as target. We now know this strain expresses a L11 LOS (as immunotyped by Hopman C, AMC lab, Netherlands) and not a L10 as had been previously thought. In other words, the reference MenA strain used for the SBA is more closely related to carriage MenA strains than to invasive MenA strains. This relationship can explain the lack of concordance observed between anti-PSA ELISA and "classical" MenA SBA in the non-primed toddler population (Example 3).

This observation reinforces the hypothesis that the lack of concordance observed between anti-PSA ELISA and F8238 MenA SBA is linked to a natural immunity acquired by the carriage of non-invasive *N. meningitidis* strains, where immunity is not directed against the polysaccharide (or at least not high avidity anti-PS antibodies) but probably against at least LOS antigens from carrier isolates.

References

Achtman M, Kusecek B, Morelli G, Eickmann K, Jianfui W, Crowe B, Wall R, Hassan-King M, Moore P and Zollinger W (1992) A comparison of the variable antigens expressed by clone IV-1 and subgroup III of *Neisseria meningitidis* serogroup A. J. Infect. Dis. 165: 53-68.

Kim J., Mandrell M, Zhen H, Westerink M, Poolman J and McLeod Griffis J (1988) Electromorphic characterization and description of conserved epitopes of the lipooligosaccharides of group A *Neisseria meningitidis*. Infect. Immun. 56: 2631-2638.

Poolman J, Hopman C and Zanen H (1982) Problems in the definition of meningococcal serotypes. FEMS Microbiol Letters 13: 339-348

Salih M, Danielsson D, Backman A, Caugant D, Achtman M and Olcen P (1990) Characterization of epidemic and non-epidemic *Neisseria meningitidis* serogroup A strains from Sudan and Sweden. J. Clin. Microbiol. 28: 1711-1719.

Scholten R, Kuipers B, Valkenburg H, Dankert J, Zollinger W and Poolman J (1994) Lipooligosaccharide immunotyping of *Neisseria meningitidis* by a whole-cell ELISA with monoclonal antibodies. J. Med. Microbiol. 41: 236-243.

Zollinger W and Mandrell R (1980) Type-specific antigens of group A *Neisseria meningitidis*: lipopolysaccharide and heat-modifiable outer membrane proteins. Infect. Immun. 28: 451-458.

Example 6

Specificity of the CDC F8238 Strain vs. Strain 3125 in an SBA Assay

Aim of the Experiment:

The impact of using *N. meningitidis* A strains with different immunotypes (here respectively the F8238 strain with L11 immunotype vs the 3125 strain with L10 immunotype) on the natural immunity observed with the MenA rSBA assay has been checked. It is to be noted that natural immunity was observed to a much lesser extent with the MenA (anti-MenA capsular polysaccharide) IgG ELISA assay. The latter assay is thus capable to differentiate between vaccine induced and naturally induced immunity.

Selected Samples:

A first set of samples was selected among studies which evaluated the immunogenicity of a booster dose of a Hib Vaccine (either conjugated or unconjugated) to children primed with pertussis (either acellular or whole cell) vaccines coadministred with Hib. In a first study performed in Germany (Hib-044) toddlers were aged between 12-18 mths and primed with different formulations of a whole cell pertussis vaccine coadministered with Hib. In a second study performed in Myanmar (Hib-064) toddlers were aged between 15-24 mths and primed with different formulations of a whole cell pertussis vaccine coadministred with Hib.

A second set of samples was selected among a study (HAV-210) which evaluated the immunogenicity of a Hepatitis A vaccine administered to children aged between 11 to 25 Mths.

Since the purpose of these studies was not to study the effect of a mena vaccination, it could therefore be anticipated that no MenA vaccine was administered to these children (they were naïve with regards to MenA vaccination). A number of samples with sufficient remaining volume to perform both MenA IgG ELISA and the two MenA rSBA assays (With L10 and L11 as assay strain) were selected at random.

Since the purpose of these studies were not to evaluate the menA groups it was not checked to exactly which groups these subjects belonged.

A third set of samples was selected among studies which evaluated different menA vaccinations. In a first study performed in the Philippines (DTPw-HepB/Hib-MenAC-TT-002) children aged approx. 10 months and 15-18 months and not previously primed with a DTPw-HepB/HibMenAC vaccine were selected. In a second study (MenACWY-TT-003) adults aged 18-25 yrs not previously vaccinated with a MenA vaccine were selected.

Results:

As clearly seen in the table below the % of subjects with a titre $>=0.30$ µg/mL with the menA IgG ELISA is very low, except for adults. The same is seen in terms of subjects $>=8$ with the MenA rSBA using the 3125 (L10) strain. The same effect is thus seen with both assays on these placebo samples i.e. they are both able to show a low response when no vaccine was administered. In contrast, performing the menA rSBA assay using the F8238 (L11) strain results in a higher % of responders ($>=8$) and as such does not reflect the fact that the subjects were not vaccinated. Therefore it is concluded that a MenA rSBA using the 3125 (L10) strain is capable to better differentiate the vaccine induced response.

| Study | Country | Age | Group | n Subset | MenA IgG ELISA % >= 0.30 µg/mL | MenA rSBA % >= 8 F8238 (L11) | MenA rSBA % >= 8 3125 (L10) |
|---|---|---|---|---|---|---|---|
| Hib-044 | Germany | 12-18 Mths | No details (Possibly all) | 68 | 5% | 39% | 2% |
| Hib-064 | Myanmar | 15-24 Mths | No details (Possibly all) | 80 | 6% | 73% | 0% |
| HAV-210 | US | 11-25 Mths | No details (Possibly all) | 92 | 0% | 30% | 0% |
| DTPw-HepB/HibMenAC-TT-002 | Philippines | Appr 10 Mths | Trit-HBV + Hib | 34 | 6% | 68% | 0% |
| DTPw-HepB/HibMenAC-TT-002 | Philippines | Appr 10 Mths | Trit-HBV/Hib + Meningitec | 39 | 5% | 77% | 21% |
| DTPw-HepB/HibMenAC-TT-002 | Philippines | 15-18 Mths | Trit-HBV + Hib | 29 | 10% | 52% | 17% |
| DTPw-HepB/HibMenAC-TT-002 | Philippines | 15-18 Mths | Trit-HBV/Hib + Meningitec | 33 | 3% | 52% | 12% |
| MenACWY-TT-003 | Belgium | 18-25 Yrs | Prior mencevax dose | 21 | 62% | 100% | 76% |
| MenACWY-TT-003 | Belgium | 18-25 Yrs | Prior MenACWY conjugate dose | 22 | 55% | 100% | 77% |

Example 7

Sensitivity of the CDC F8238 Strain vs. Strain 3125 in an SBA Assay

Clinical trial samples were selected among studies which evaluated different menA vaccinations. In a first study performed in the Philippines naïve children aged approx. 14 weeks were primed with one of three different DTPw-HepB/HibMenAC vaccine formulations (where HibMenAC are all conjugated). Seroconversion (% SC) was measured as the % of children 1 month post priming with an rSBA (50%) titre more than or equal to 8.

| rSBA strain | rSBA GMTs | | rSBA % SC | |
| --- | --- | --- | --- | --- |
| | F8238 | 3125 | F8238 | 3125 |
| Vaccine 1 | 315 | 160 | 94 | 88 |
| Vaccine 2 | 400 | 229 | 100 | 100 |
| Vaccine 3 | 284 | 156 | 100 | 100 |

Clinical trial samples were also selected among studies which evaluated different menACYW vaccinations. In a study performed in the Belgium naïve adults (not previously immunized with a menA vaccine) aged 18-25 years were primed with either a unconjugated menACWY capsular polysaccharide vaccine (Mencevax™—GSKBiologicals s.a.) or a conjugated menACWY vaccine. Seroconversion (% SC) was measured as the % of adults 1 month post immunisation with a 4 fold increase in rSBA (50%) titre compared with just prior to immunisation.

| rSBA strain | rSBA GMTs | | rSBA % SC | |
| --- | --- | --- | --- | --- |
| | F8238 | 3125 | F8238 | 3125 |
| Mencevax™ | 6776 | 2875 | 88 | 100 |
| Conjugate | 4626 | 2121 | 53 | 89 |

The data show that the 3125 strain is sensitive to vaccine induced antibodies from either conjugated or unconjugated menA capsular polysaccharide vaccines. In addition it is possible (for instance in older age groups beyond 3 years of age) that the % SC data produced with the 3125 strain may be more accurate than with the F8238 strain.

Deposited Materials

The *N. menigitidis* serogroup A strain F8238 is available from the Centers for Disease Control and Prevention (CDC), Atlanta, Ga., USA. Alternatively it has also been deposited at the Belgian Coordinated Collections of Microorganisms (BCCM), Laboratorium voor Microbiologie-Bacterien-verzameling (BCCM/LMG), Universiteit Gent, K. L. Ledeganckstraat 35, 9000 GHENT, Belgium (deposited 20 Jun. 2005 with a statement that it is equivalent to the CDC MenA F8238 strain). It has the Accession Number LMG P-23098.

The *N. meningitidis* serogroup A strain 3125 is available from the Academic Medical Center (AMC), University of Amsterdam, Netherlands Reference Laboratory for Bacterial Meningitis, Dept. of Medical Microbiology, Meibergdreef 15, 1105 AZ Amsterdam, The Netherlands. Alternatively it has also been deposited at the Belgian Coordinated Collections of Microorganisms (BCCM), Laboratorium voor Microbiologie-Bacteriënverzameling (BCCM/LMG), Universiteit Gent, K. L. Ledeganckstraat 35, 9000 GHENT, Belgium (deposited 20 Jun. 2005 with a statement that it is equivalent to the AMC MenA 3125 strain). It has the Accession Number LMG P-23097.

The *N. meningitidis* serogroup A strain 3048 (A:NT:P1.6:L3,6) is available from the Academic Medical Center (AMC), University of Amsterdam, Netherlands Reference Laboratory for Bacterial Meningitis, Dept. of Medical Microbiology, Meibergdreef 15, 1105 AZ Amsterdam, The Netherlands. Alternatively it has also been deposited at the European Collection of Cell Cultures (ECACC), Health Protection Agency, Porton Down, Salisbury, SP4 0JG, UK (Accession Number: 04070702). The strain was deposited on 21 Jun. 2004.

The *N. meningitidis* serogroup W strain S4383 is available from the Centers for Disease Control and Prevention (CDC), Atlanta, Ga., USA. Alternatively it has also been deposited at the Belgian Coordinated Collections of Microorganisms (BCCM), Laboratorium voor Microbiologie-Bacteriën-verzatneling (BCCM/LMG), Universiteit Gent, K. L. Ledeganckstraat 35, 9000 GHENT, Belgium (deposited 20 Jun. 2005 with a statement that it is equivalent to the CDC MenW S4383 strain). It has the Accession Number LMG P-23099.

The *N. meningitidis* serogroup W strain 3193 (W135:2A:P1.5,2:L3) is available from the Academic Medical Center (AMC), University of Amsterdam, Netherlands Reference Laboratory for Bacterial Meningitis, Dept. of Medical Microbiology, Meibergdreef 15, 1105 AZ Amsterdam, The Netherlands. Alternatively it has also been deposited at the European Collection of Cell Cultures (ECACC), Health Protection Agency, Porton Down, Salisbury, SP4 0JG, UK (Accession Number: 04070701). The strain was deposited on 21 Jun. 2004.

The deposit of the deposited strain has been made under the terms of the Budapest Treaty on the International Recognition of the Deposit of Micro-organisms for Purposes of Patent Procedure. The deposited strain will be irrevocably and without restriction or condition released to the public upon the issuance of a patent. The deposited strain is provided merely as convenience to those of skill in the art and is not an admission that a deposit is required for enablement, such as that required under 35 U.S.C. §112; A license may be required to make, use or sell the deposited strain and no such license is hereby granted.

We claim:

1. A *N. meningitides* serotype W Serum Bactericidal Activity (SBA) assay comprising the step of determining the SBA titre of a serum sample against a *N. meningitides* serotype W reference strain, wherein said serum sample has been taken from a host immunized with a vaccine composition comprising a capsular polysaccharide antigen from *N. meningitides* serogroup W, and said serotype W reference strain has a percent complement toxicity of less than 5% when measured using baby rabbit complement, or a percent complement toxicity less than that of the S4383 standard reference strain when measured using baby rabbit complement.

2. The *N. meningitidis* serogroup W Serum Bactericidal Activity (SBA) assay of claim 1, wherein the *N meningitidis* serogroup W reference strain is isolate 3193.

3. A *N. meningitidis* serotype W Serum Bactericidal Activity (SBA) assay of claim 1, wherein the serum sample has been taken from a human aged 0-55 years.

4. A kit for carrying out the SBA assays of claim 1 comprising the *N. meningitidis* serotype W reference strain of claim 1 and instructions for its use in an SBA assay.

5. The SBA assay of claim 1 which is a human SBA (hSBA) assay.

6. The SBA assay of claim 1 which is a rabbit SBA (rSBA) assay.

7. A *N. meningitidis* serotype W Serum Bactericidal Activity (SBA) assay of claim 1, wherein the serum sample has been taken from a human aged 1 month-20 years.

8. A *N. meningitidis* serotype W Serum Bactericidal Activity (SBA) assay of claim 1, wherein the serum sample has been taken from a human aged 0-2 years.

9. A kit for carrying out a *N. meningitidis* serotype W Serum Bactericidal Activity (SBA) assay, comprising *N. meningitidis* serotype W isolate 3193 and instructions for its use in an SBA assay.

* * * * *